(12) United States Patent
Kuroi et al.

(10) Patent No.: US 11,318,478 B2
(45) Date of Patent: May 3, 2022

(54) ELECTRIC DISCHARGE DEVICE AND AIR PURIFYING DEVICE

(71) Applicant: DAIKIN INDUSTRIES, LTD., Osaka (JP)

(72) Inventors: Kiyoshi Kuroi, Osaka (JP); Kei Suzumura, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 225 days.

(21) Appl. No.: 16/327,234

(22) PCT Filed: Aug. 4, 2017

(86) PCT No.: PCT/JP2017/028443
§ 371 (c)(1),
(2) Date: Feb. 21, 2019

(87) PCT Pub. No.: WO2018/061483
PCT Pub. Date: Apr. 5, 2018

(65) Prior Publication Data
US 2019/0210038 A1    Jul. 11, 2019

(30) Foreign Application Priority Data

Sep. 30, 2016  (JP) .............................. JP2016-194907

(51) Int. Cl.
*B03C 3/41*    (2006.01)
*A61L 9/22*    (2006.01)
(Continued)

(52) U.S. Cl.
CPC ................. *B03C 3/41* (2013.01); *A61L 9/22* (2013.01); *F24F 7/00* (2013.01); *H01T 19/04* (2013.01); *H01T 23/00* (2013.01); *B03C 2201/10* (2013.01)

(58) Field of Classification Search
CPC ... B03C 3/41; B03C 2201/10; B03C 2201/08; B03C 3/64; B03C 2201/06; B03C 23/62;
(Continued)

(56) References Cited

U.S. PATENT DOCUMENTS

| 1,992,113 A | 2/1935 | Anderson |
| 2004/0237788 A1* | 12/2004 | Mischkulnig ............. B03C 3/41 96/95 |
| 2006/0272505 A1* | 12/2006 | Tanaka ...................... B03C 3/41 96/96 |

FOREIGN PATENT DOCUMENTS

| EP | 3 089 292 A1 | 11/2016 |
| JP | 51-111280 | 9/1976 |

(Continued)

OTHER PUBLICATIONS

International Search Report issued in PCT/JP2017/028443 (PCT/ISA/210), dated Oct. 31, 2017.

*Primary Examiner* — Xiuyu Tai
(74) *Attorney, Agent, or Firm* — Birch, Stewart, Kolasch & Birch, LLP (57) ABSTRACT

A shaft member has the same polarity as discharge electrodes. Each of the discharge electrodes has an electrode body and a tip end which is formed at an end of the electrode body facing an inner peripheral surface of a counter electrode. The discharge electrodes extend such that the tip ends and the electrode bodies are misaligned with each other in an axial direction of the shaft body. A streamer discharge travels from the tip ends of the discharge electrodes toward the inner peripheral surface of the counter electrode.

9 Claims, 8 Drawing Sheets

(51) Int. Cl.
*H01T 19/04* (2006.01)
*H01T 23/00* (2006.01)
*F24F 7/00* (2021.01)

(58) Field of Classification Search
CPC .. B03C 23/47; B03C 3/49; B03C 3/51; B03C
2201/14; B03C 3/70; B03C 3/06; B03C
2201/12; B03C 2201/30; A61L 9/22;
F24F 7/00; H01T 19/04; H01T 23/00;
Y10S 55/38; B01D 53/32; B01J 19/088;
B01J 2219/0835; B01J 2219/0828; B01J
2219/0822; B01J 2219/0813; B05D 5/12;
H01J 9/04; F01N 3/01; F01N 3/0275
See application file for complete search history.

(56) References Cited

FOREIGN PATENT DOCUMENTS

| | | | |
|---|---|---|---|
| JP | 2001-38243 | A | 2/2001 |
| JP | 2002-126573 | A | 5/2002 |
| JP | 2002-233789 | A | 8/2002 |
| JP | 2005-80835 | A | 3/2005 |
| JP | 2009-142808 | A | 7/2009 |
| JP | 2013-124556 | A | 6/2013 |
| JP | 5761424 | B2 | 8/2015 |

* cited by examiner

ELECTRIC DISCHARGE DEVICE AND AIR PURIFYING DEVICE

TECHNICAL FIELD

The present invention relates to an electric discharge device and an air purification device including the same.

BACKGROUND ART

Conventionally, there has been known an electric discharge device which is mounted on an air purification device or the like, and performs a streamer discharge.

The electric discharge device disclosed in Patent Document 1 includes a plurality of discharge electrodes and a counter electrode facing the discharge electrodes. The plurality of discharge electrodes are formed in a rod shape parallel to the counter electrode. These discharge electrodes are supported at the side edges of a rectangular parallelepiped base portion, and are arranged at predetermined intervals in a longitudinal direction of the base portion.

When a voltage is applied from a power supply to the discharge electrodes and the counter electrode, a streamer discharge occurs from the tip ends of the plurality of discharge electrodes toward the counter electrode. Active species, when generated in the air through the streamer discharge, is utilized for decomposing harmful substances (such as odor components and allergens) in the air.

CITATION LIST

Patent Document

[Patent Document 1] Japanese Patent No. 5761424

SUMMARY OF THE INVENTION

Technical Problem

In the electric discharge device disclosed in Patent Document 1, the discharge electrodes are arranged at predetermined intervals in the longitudinal direction of the base portion, resulting in the increase in the size of the electric discharge device in the longitudinal direction. On the other hand, if the interval between the discharge electrodes is made too small in order to downsize the electric discharge device, electric fields around the discharge electrodes may interfere with each other, and thus, a stable streamer discharge may not be generated.

In view of the foregoing background, it is therefore an object of the present invention to provide an electric discharge device which is compact and capable of generating a stable streamer discharge, and an air purification device including the electric discharge device.

Solution to the Problem

A first aspect of the invention is directed to an electric discharge device including: a shaft member (32); a plurality of discharge electrodes (60) arranged in a circumferential direction around an axis of the shaft member (32); a cylindrical counter electrode (20) in which the shaft member (32) and the discharge electrodes (60) are arranged; and a power supply (81) applying a voltage to the discharge electrodes (60) and the counter electrode (20), wherein the shaft member (32) has the same polarity as the discharge electrodes (60), each of the discharge electrodes (60) has an electrode body (65) and a tip end (63) which is formed at an end of the electrode body (65) facing an inner peripheral surface (21) of the counter electrode (20), the discharge electrodes (60) extending such that the tip ends (63) and the electrode bodies (65) are misaligned with each other in an axial direction of the shaft body (32), and a streamer discharge travels from the tip ends (63) of the discharge electrodes (60) toward the inner peripheral surface (21) of the counter electrode (20).

According to the first aspect of the present invention, the plurality of discharge electrodes (60) are arranged in the circumferential direction on the outer peripheral surface (43) of the shaft member (32), and the inner peripheral surface (21), which is cylindrical, of the counter electrode (20) is formed on the outer peripheral side of the plurality of discharge electrodes (60). When a voltage is applied from the power supply (81) to the discharge electrodes (60) and the counter electrode (20), a streamer discharge occurs radially outward from the tip ends of the discharge electrodes (60) toward the inner peripheral surface (21) of the counter electrode (20). With the discharge electrodes (60) arranged in the circumferential direction in this manner, active species can be generated with high density without increasing the size of the discharge electrodes in the longitudinal direction as in the case of the prior art.

In addition, according to the present invention, since the tip ends (63) of the discharge electrodes (60) and the electrode body (65) are misaligned with each other in the axial direction of the shaft member (32), a space extending in the radial direction is formed between the tip ends (63) of the discharge electrodes (60) and the outer peripheral surface (43) of the shaft member (32). Since the outer peripheral surface (43) of the shaft member (32) has the same polarity as the discharge electrodes (60), an electric field that allows a streamer discharge to travel radially outward is formed in this space. That is, this electric field causes the discharge occurring from the tip ends (63) of the discharge electrodes (60) not to travel toward the shaft member (32), but to be directed away from the shaft member (32) (i.e., toward the counter electrode (20)). This can stably cause a radial streamer discharge from the tip ends (63) of the discharge electrodes (60) toward the counter electrode (20).

A second aspect of the invention is an embodiment of the first aspect. In the second aspect, a plurality of electrode rows (L) each having the discharge electrodes (60) arranged in the circumferential direction are arranged in the axial direction of the shaft member (32).

According to the second aspect of the invention, a radial discharge region formed in each of the electrode rows is enlarged in the axial direction of the shaft member (32), and thus, the region in which the active species is generated is also enlarged.

A third aspect of the invention is an embodiment of the first or second aspect. In the third aspect, the discharge electrodes (60) extend to form a predetermined angle with a plane perpendicular to an axis of the shaft member (32).

According to the third aspect of the invention, the discharge electrodes (60) do not extend radially outward toward the counter electrode (20), but extend to form a predetermined angle with the plane perpendicular to the axis of the shaft member (32). Thus, the tip ends (63) of the discharge electrodes (60) are positioned close to the center of the shaft. Therefore, even if the inner peripheral surface (21) of the counter electrode (20) is reduced in diameter, a sufficient distance can be ensured between the tip ends (63) of the discharge electrodes (60) and the counter electrode (20).

If the discharge electrodes (60) are configured to extend radially outward along the plane perpendicular to the axis, a distance between the discharge electrodes (60) and the counter electrode (20) greatly varies when the tip ends (63) of the discharge electrodes (60) are melted and shifted toward base portions of the discharge electrodes (60). According to the present invention, in contrast, the discharge electrodes (60) extend to form a predetermined angle with respect to the plane perpendicular to the axis. Thus, even if the tip ends (63) of the discharge electrodes (60) are shifted toward the base portions, the distance between the electrodes does not greatly vary. This can cause a streamer discharge stably for a long time.

A fourth aspect of the invention is an embodiment of the second aspect. In the fourth aspect, each of the discharge electrodes (60) extends obliquely to approach the inner peripheral surface (21) of the counter electrode (20) as the discharge electrode (60) goes toward the tip end (63).

According to the fourth aspect of the invention, even if the tip ends (63) of the discharge electrodes (60) are melted, the distance between the electrodes does not greatly vary because the tip ends (63) are shifted obliquely with respect to the plane perpendicular to the axis. This can cause a streamer discharge stably for a long time.

When the discharge electrodes (60) are arranged to extend obliquely in this manner, a distance between the discharge electrodes (60) in an adjacent pair of the electrode rows (L) can be increased. Specifically, in this configuration, the distance between the tip ends (63) of the discharge electrodes (60) in one of the adjacent pair of the electrode rows (L) and the base portions of the discharge electrodes (60) in the other electrode row (L) increases, thereby increasing the pitch between the electrode rows (L). This can downsize the electric discharge device (10) in the axial direction.

A fifth aspect of the invention is an embodiment of the first or second aspect. In the fifth aspect, the discharge electrodes (60) extend along an axial direction of an inner peripheral surface (21) of the counter electrode (20).

According to the fifth aspect of the invention, even if the tip ends (63) of the discharge electrodes (60) are melted, the distance between the electrodes hardly vary because the tip ends (63) are shifted in a direction parallel to the inner peripheral surface (21) of the counter electrode (20). This can cause a streamer discharge stably for a long time.

A sixth aspect of the invention is an embodiment of any one of the third to fifth aspects. In the sixth aspect, an air flow path (12) through which air flows in the axial direction of the shaft member (32) is formed between the shaft member (32) and the counter electrode (20), and the discharge electrodes (60) extend so that the tip ends (63) face toward a downstream side in a flow direction of the air.

According to the sixth aspect of the invention, the discharge electrodes (60) extend downstream in the direction of the air flow, and the discharge electrodes (60) are less likely to be a resistance to the air flow path. This can reduce the pressure loss in the air flow path.

A seventh aspect of the invention is an embodiment of the second aspect. In the seventh aspect, the tip ends (63) of the discharge electrodes (60) in one of the electrode rows (L) and the tip ends (63) of the discharge electrodes (60) of another electrode row (L) adjacent to the one of the electrode row (L) are misaligned with each other in a circumferential direction when viewed in the axial direction of the shaft member (32).

According to the seventh aspect of the present invention, the tip ends (63) of the discharge electrodes (60) in one of an adjacent pair of the electrode rows (L) are misaligned in the circumferential direction with the tip ends (63) of the discharge electrodes (60) in the other electrode row (L). Thus, the distance between the tip ends (63) of the discharge electrodes (60) in one of the adjacent pair of the electrode rows (L) and the tip ends (63) of the discharge electrodes (60) in the other electrode row (L) increases, which can reduce the pitch between the electrode rows (L). This can downsize the electric discharge device (10) in the axial direction.

An eighth aspect of the invention is an embodiment of any one of the first to seventh aspects. In the eighth aspect, the tip ends (63) of the discharge electrodes (60) are arranged at equal intervals around an axis of the shaft member (32).

According to the eighth aspect of the present invention, the pitches between the tip ends (63) of the plurality of discharge electrodes (60) are equal to each other, and electric fields around the discharge electrodes (60) are made uniform. This can cause a radial streamer discharge more stably.

A ninth aspect of the invention is directed to an air purification device, and the air purification device includes the electric discharge device (10) of any one of the first to eighth aspects.

According to the ninth aspect of the present invention, an air purification device including a compact electric discharge device capable of stably generating a streamer discharge can be provided.

Advantages of the Invention

According to the first aspect of the present invention, a radial streamer discharge can be generated from the plurality of discharge electrodes (60) arranged in the circumferential direction toward the counter electrode (20), and thus, a compact electric discharge device capable of stably generating a streamer discharge can be provided.

In a configuration in which a plurality of discharge electrodes (60) are arranged in the circumferential direction, a single discharge electrode (60) is arranged on each side of every discharge electrode (60). Further, the tip ends (63) of all the discharge electrodes (60) have the same positional relationship relative to the inner peripheral surface (21) of the counter electrode (20) and the outer peripheral surface (43) of the shaft member (32). Therefore, electric fields around the discharge electrodes (60) can be made uniform, and a uniform and stable radial streamer discharge can be achieved.

According to the second aspect of the present invention, the discharge region can be enlarged in the axial direction of the shaft member (32), which can increase the amount of active species to be generated.

According to the third aspect of the present invention, the diameter of the counter electrode (20) can be reduced, and the electric discharge device (10) can be made more compact. Further, the change in the distance between the electrodes caused by the shift of the tip ends (63) of the discharge electrodes (60) can be reduced. In particular, according to the fourth aspect of the present invention, the pitch between the electrode rows (L) can be reduced, and the electric discharge device (10) can further be downsized. According to the fifth aspect of the present invention, the change in the distance between the electrodes caused by the shift of the tip ends (63) of the discharge electrodes (60) can be almost prevented.

According to the sixth aspect of the present invention, the resistance of the air flow path (12) can be reduced.

According to the seventh aspect of the present invention, the pitch between the electrode rows (L) can further be reduced, and the electric discharge device (10) can further be downsized.

According to the eighth aspect of the present invention, the radial streamer discharge can be made more uniform and stable.

DESCRIPTION OF EMBODIMENTS

Embodiments of the present disclosure will be described in detail with reference to the drawings. The embodiment described below is merely an exemplary one in nature, and is not intended to limit the scope, applications, or use of the invention.

Embodiment of the Invention

An electric discharge device (10) according to the present invention is used for an air cleaner (1) (air purification device) which handles the air in a room of a house, for example.

<General Configuration of Air Cleaner>

Figure 1:
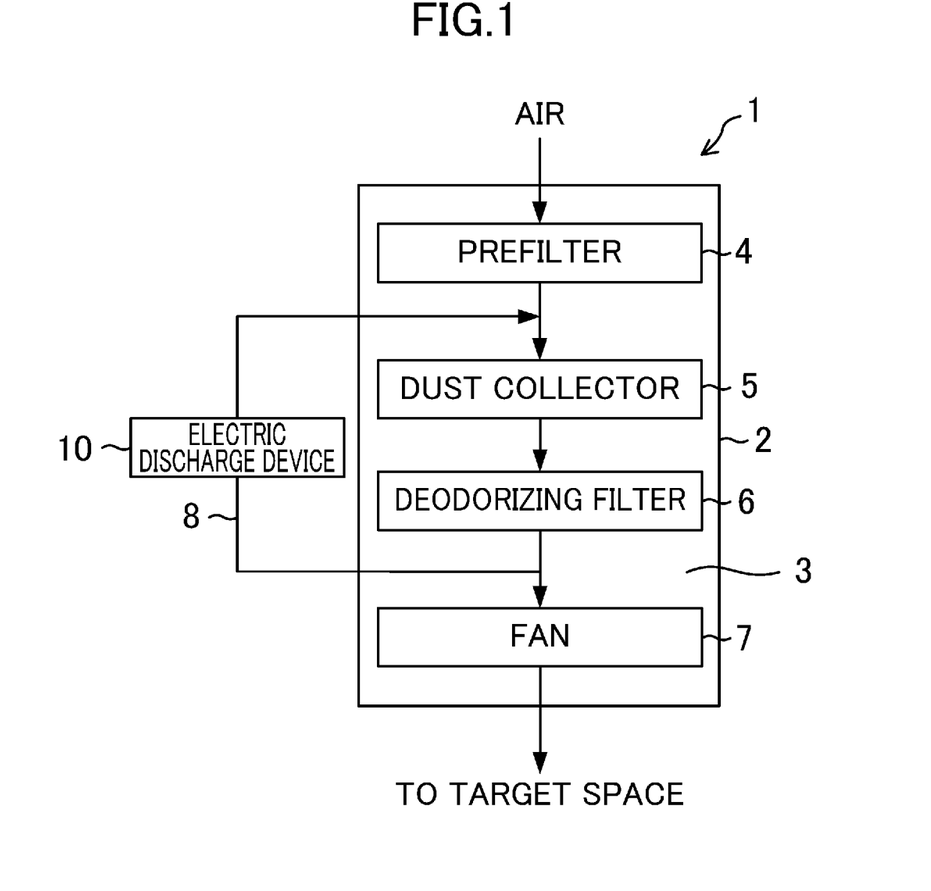
FIG. 1 is a block diagram showing a schematic configuration of an air purification device according to an embodiment.

As schematically shown in FIG. 1, the air cleaner (1) includes a hollow casing (2). An air handling passage (3) into which the air is introduced is formed inside the casing (2). Functional components for processing the air are disposed in the air handling passage (3). For example, in the air handling passage (3), a prefilter (4), a dust collector (5), a deodorizing filter (6), and a fan (7) are provided in this order from the upstream to downstream of the direction of an air flow. An inflow end of a return flow path (8) is connected to a flow path between the deodorizing filter (6) and the fan (7). An outflow end of the return flow path (8) is connected to a flow path between the prefilter (4) and the dust collector (5). The electric discharge device (10) is provided for the return flow path (8).

The prefilter (4) catches relatively large dust in the air. The dust collector (5) is configured as an electric dust collector which electrically collects relatively small dust in the air. The deodorizing filter (6) includes a catalyst and an adsorbent supported on a surface of a honeycomb base material, for example. The fan (7) conveys target air (e.g., indoor air) sucked into the air handling passage (3) in the casing (2). The electric discharge device (10) generates active species for removing harmful substances in the air through discharge. The active species generated in the electric discharge device (10) in the return flow path (8) is supplied to the air handling passage (3) upstream of the dust collector (5) and used to decompose harmful substances, bacteria, and viruses in the air. The air that has passed through the prefilter (4), the dust collector (5), and the deodorizing filter (6) in this order is supplied to a target space (e.g., an indoor space).

Note that the air cleaner (1) may be configured without the return flow path (8) of FIG. 1, and the electric discharge device (10) may be disposed between the dust collector (5) and the deodorizing filter (6).

<Electric Discharge Device>

Details of the structure of the electric discharge device (10) will be described below with reference to FIGS. 2 to 9. The electric discharge device (10) includes a case unit (11) (case member), a counter electrode (20) and a discharge unit (30) both housed in the case unit (11). The electric discharge device (10) includes discharge electrodes (60) of the discharge unit (30), and a power supply unit (80) for applying a voltage to the counter electrode (20).

<Case Unit>

Figure 2:
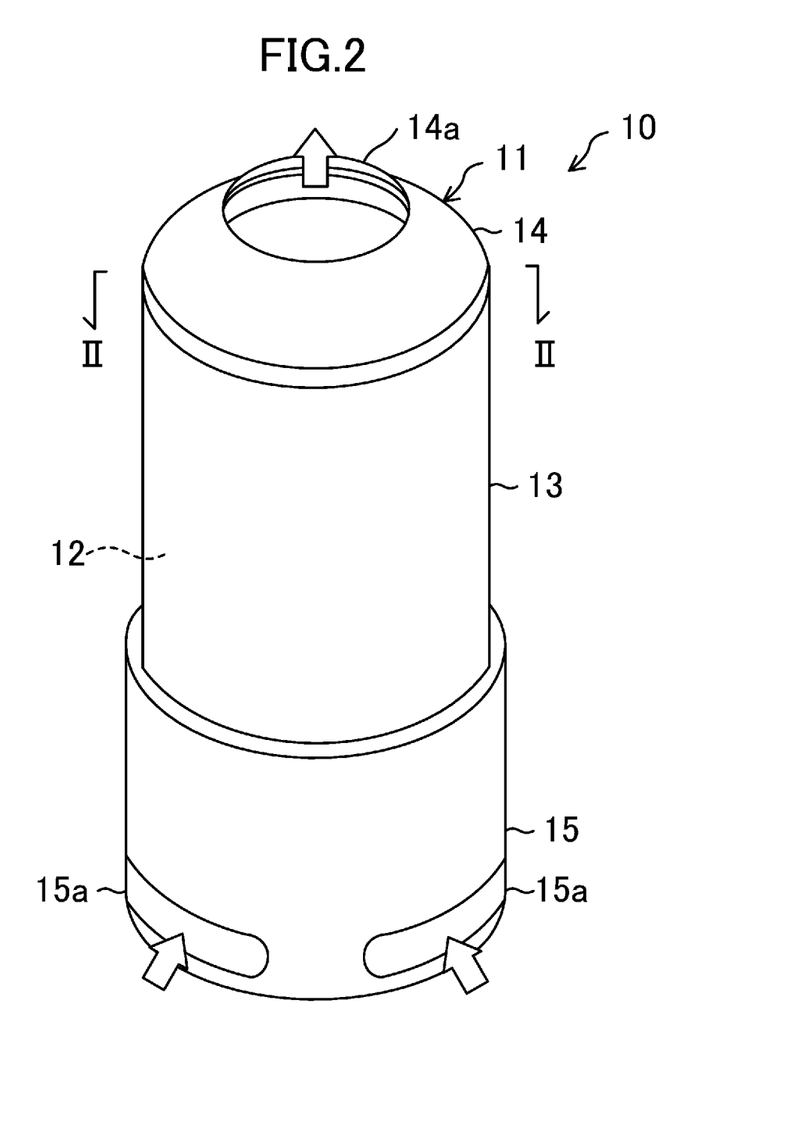
FIG. 2 is a perspective view showing an external appearance of an electric discharge device.
Figure 3:
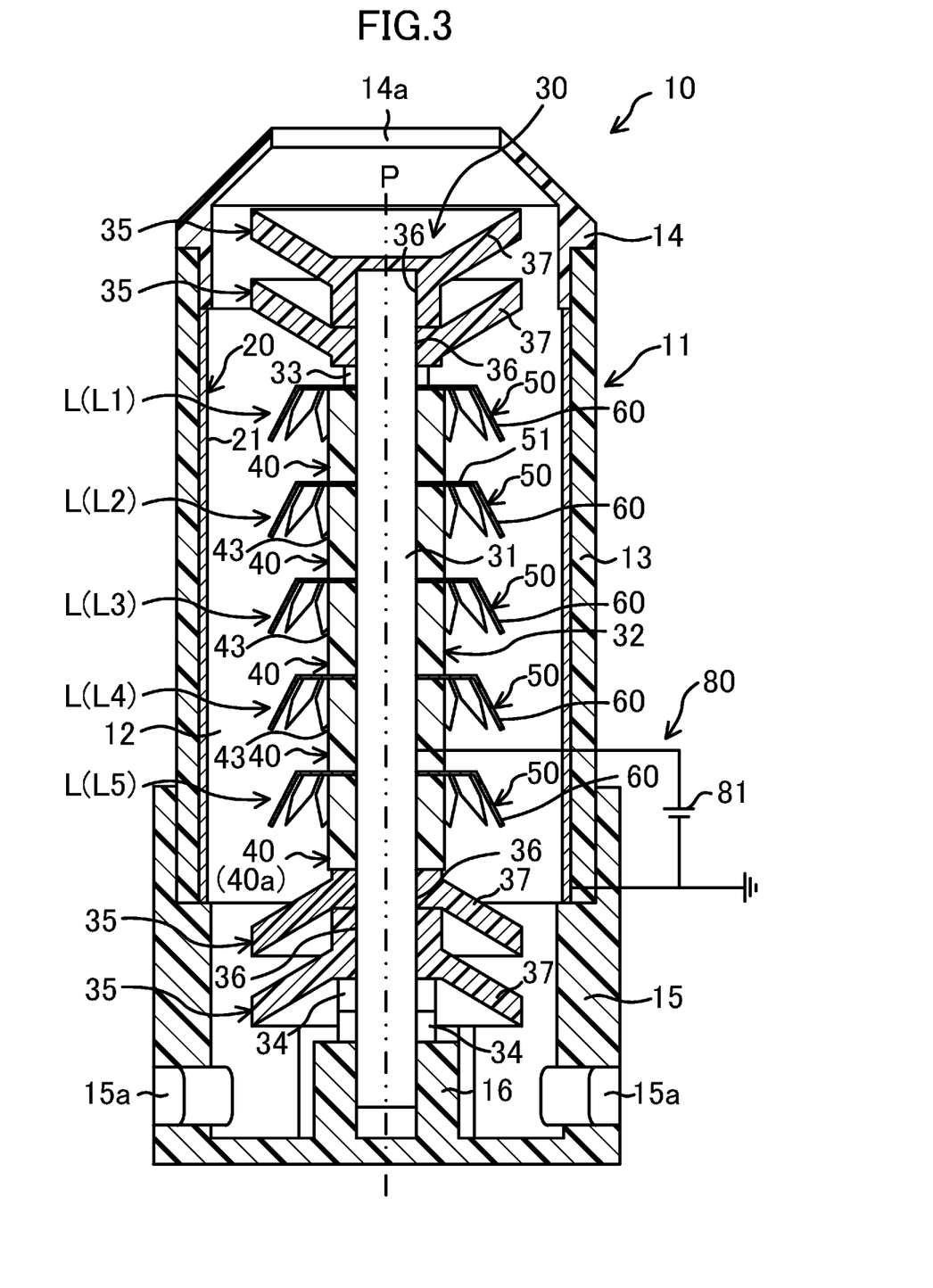
FIG. 3 is a cross-sectional view taken along line II-II of FIG. 2.

As shown in FIGS. 2 and 3, the case unit (11) is configured as a vertically long hollow insulating member. An air flow path (12) through which the air flows is formed in the case unit (11). The case unit (11) has a cylindrical barrel (13), a first lid (14), and a second lid (15). The barrel (13) is formed in a cylindrical shape with both ends opened. The first lid (14) is provided on one end of the barrel (13) in an axial direction (an upper side in FIG. 3). The second lid (15) is provided on the other end of the barrel (13) in the axial direction (a lower side in FIG. 3).

The first lid (14) is in the shape of a truncated conical cylinder which is tapered upward. A substantially circular outflow port (14a) is formed through the top of the first lid (14).

A plurality of (e.g., three) inflow ports (15a) are formed through a lower portion of an outer peripheral wall of the second lid (15). Each inflow port (15a) is formed as a horizontally elongated opening extending in a circumferential direction along the outer peripheral wall of the second lid (15). The plurality of inflow ports (15a) are arranged at equal intervals in the circumferential direction. A shaft support (16) for supporting a shaft body (31) (shaft portion) of the discharge unit (30) is formed on a bottom wall of the second lid (15). The shaft support (16) is formed in a cylindrical shape protruding upward from the center of the bottom wall of the second lid (15), and an end portion (lower end portion) of the shaft body (31) is inserted into the shaft support (16).

<Counter Electrode>

As shown in FIG. 3, the counter electrode (20) is disposed inside the barrel (13) of the case unit (11). The counter electrode (20) is made of a conductive material (e.g., a metal material) which is cylindrical and fitted into the barrel (13). The counter electrode (20) has an inner peripheral surface (21) which is in the shape of a tube (more strictly, a cylinder). The inner peripheral surface (21) serves as a facing surface which faces the plurality of discharge electrodes (60). The counter electrode (20) is supported by the case unit (11) so that the axis of the inner peripheral surface (21) coincides with an axis (P) of the shaft body (31).

<Discharge Unit>

Figure 4:
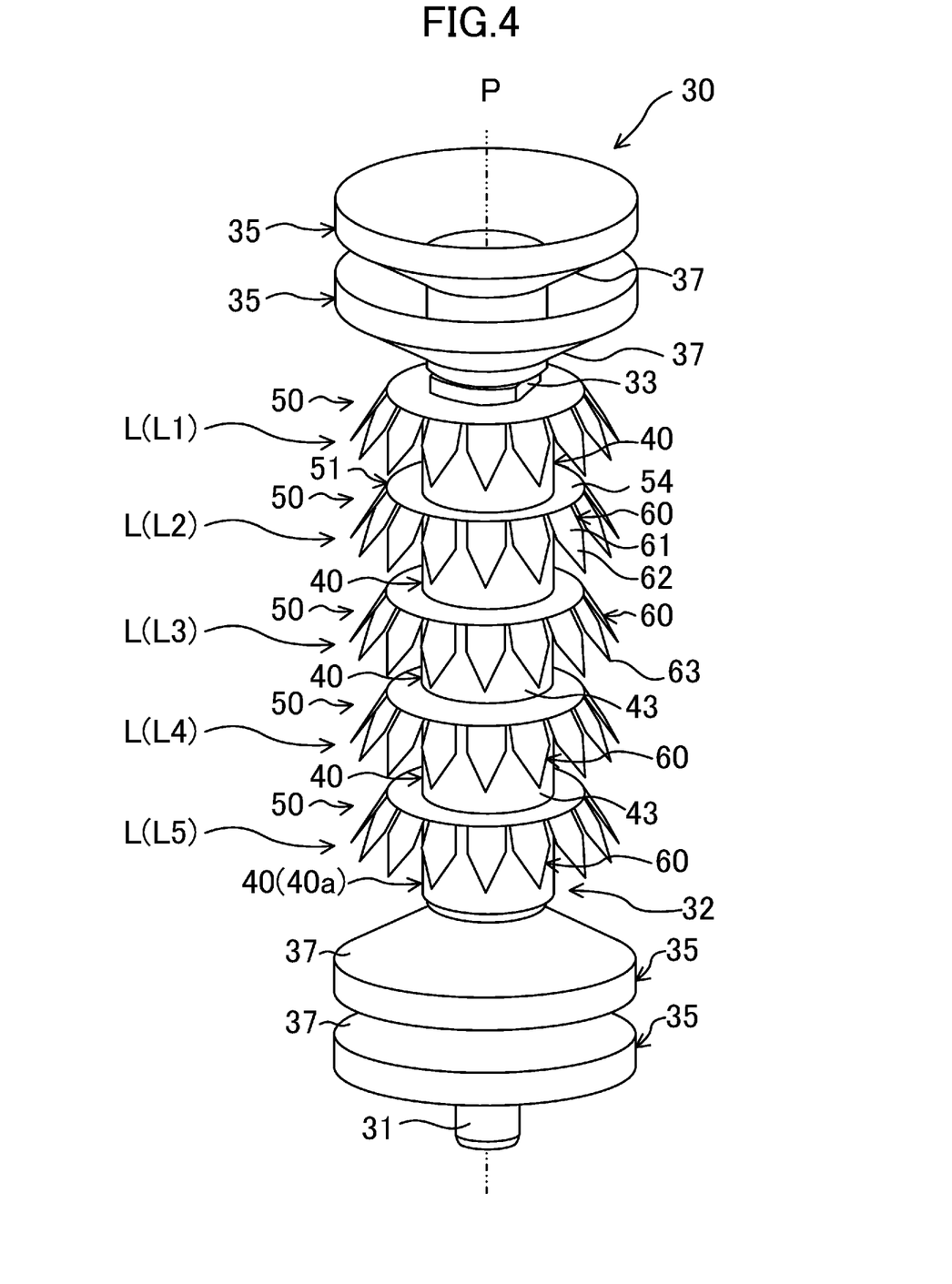
FIG. 4 is a perspective view showing a general configuration of a discharge unit.
Figure 5:
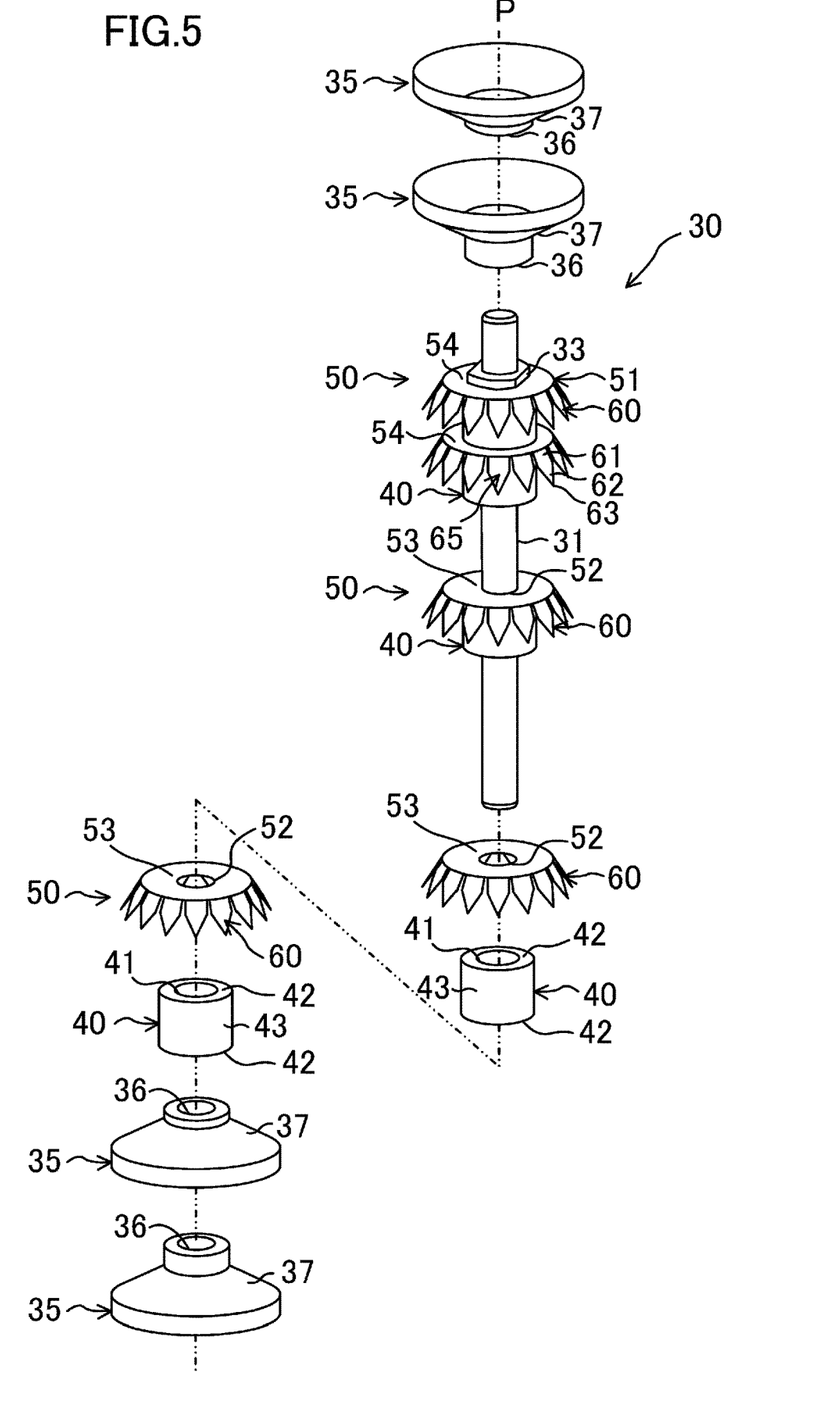
FIG. 5 is an exploded perspective view showing an example of the discharge unit in an assembled state.

As shown in FIGS. 3 to 5, the discharge unit (30) includes a single shaft body (31), a plurality of (four in this example) insulators (35), a plurality of (five in this example) spacers (40), and a plurality of (five in this example) discharge members (50). The shaft body (31) penetrates the spacers (40), the insulators (35), and the discharge members (50), which are detachably attached to the shaft body (31) (see FIG. 5). The shaft body (31) and the spacers (40) form a shaft member (32). The shaft body (31) is configured as a shaft portion extending across the plurality of spacers (40).

[Shaft Body]

The shaft body (31) is configured as a columnar strut extending upward from the shaft support (16) of the second lid (15). The shaft body (31) is made of a conductive material (e.g., a metal material) which is electrically connected to a positive electrode side of the power supply (81). Note that the shaft body (31) may be electrically connected to a negative electrode side of the power supply (81).

An annular stopper (33) having a larger diameter than the shaft body (31) is fixed to an upper portion of the shaft body (31). For example, two nuts (34) are screwed onto a lower portion of the shaft body (31). With the insulators (35), the spacers (40), and the discharge members (50) attached to the shaft body (31), the two nuts (34) are fastened. Thus, the insulators (35), the spacers (40), and the discharge members (50) are sandwiched between the stopper (33) and the two nuts (34).

[Insulator]

The insulators (35) each constitute an insulating member made of a ceramic material. The insulators (35) are disposed at both ends of the shaft body (31). Specifically, two of the insulators (35) are arranged between the shaft support (16) and the lowermost spacer (40) on the shaft body (31). The other two insulators (35) are arranged between the shaft support (16) and the uppermost spacer (40) on the shaft body (31). Each of the insulators (35) is provided with an insulator-side receiving portion (36) at its center through which the shaft body (31) is inserted. Each insulator (35) has a flared portion (37) whose outer diameter increases toward the end of the shaft body (31). This flared portion (37) increases the creepage distance of the insulator (35).

[Spacer]

Five spacers (40) are arranged in the axial direction between the upper insulators (35) and the lower insulators (35). Specifically, the lowermost one (also referred to as a "lowermost spacer (40a)") of the five spacers (40) is disposed between the insulators (35) and a support plate portion (51) of the lowermost discharge member (50). Four of the five spacers (40) except for the lowermost spacer (40a) are each disposed between the support plate portions (51) of an adjacent pair of the discharge members (50).

The spacers (40) are made of, for example, a conductive resin material. Each spacer (40) is formed in a cylindrical shape, and a spacer-side receiving portion (41) (receiving portion) is formed along its axis so that the shaft body (31) is inserted therein. Annular planes (42) are formed at both axial ends (upper and lower ends) of each of the spacers (40).

Each spacer (40) has a cylindrical outer peripheral surface (43). The outer peripheral surface (43) faces tip ends (63) of the discharge electrodes (60), and constitutes a discharge stabilizer for stabilizing a streamer discharge from the tip ends (63) of the discharge electrodes (60) toward the counter electrode (20). This will be described later in detail. Further, each of the spacers (40) determines the relative positions of (interval between) electrode rows (L) (the discharge members (50)) adjacent to each other.

[Discharge Member]

As shown in FIGS. 5 to 9, each of the discharge members (50) includes the support plate portion (51) (support portion) and the plurality of discharge electrodes (60) supported on an outer peripheral edge of the support plate portion (51). The support plate portion (51) and the discharge electrodes (60) are integrally formed by pressing, for example, a sheet metal.

Figure 8:
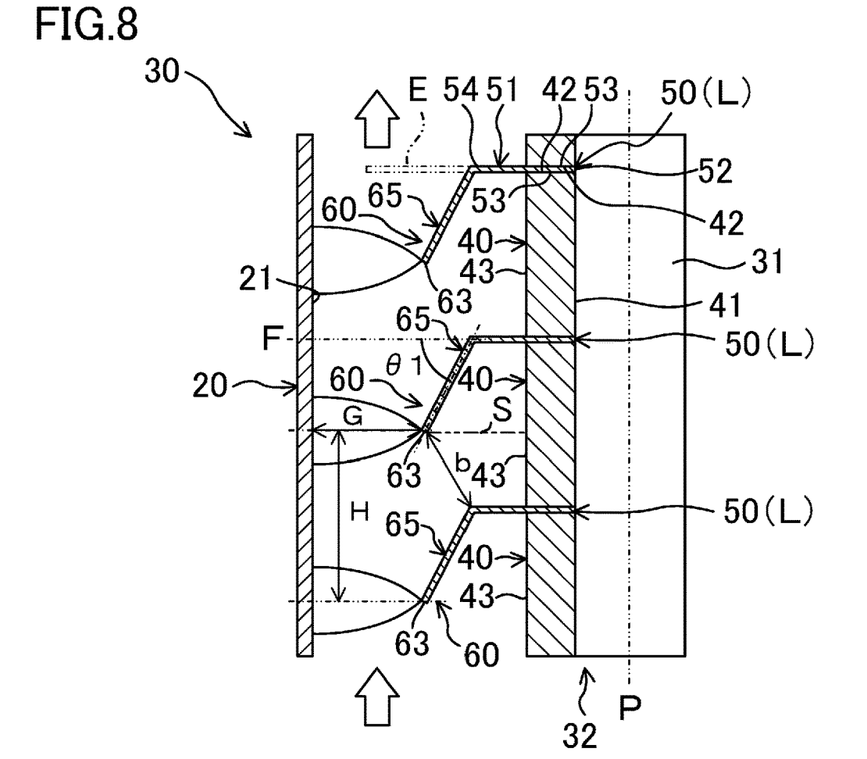
FIG. 8 is an enlarged longitudinal cross-sectional view of a major portion of the discharge unit.

The support plate portion (51) is in the shape of a flat plate extending along a plane (a virtual plane (F) shown in FIG. 8) perpendicular to the axis (P). The support plate portion (51) has a circular fitting hole (52) into which the shaft body (31) is fitted. Upper and lower surfaces of the support plate portion (51) serve as annular contact surfaces (53) each of which makes surface contact with the plane (42) of the spacer (40). In other words, the support plate portion (51) is supported with the upper and lower contact surfaces (53) respectively abutting on the planes (42) of the upper and lower spacers (40). Thus, flatness of the support plate portion (51) can be maintained with high accuracy.

The support plate portion (51) has a larger outer diameter than the spacer (40). Thus, the support plate portion (51) extends further radially outward from the outer peripheral surface (43) of the spacer (40). This projecting portion constitutes an annular projecting plate portion (54).

The discharge member (50) of the present embodiment has, for example, 15 discharge electrodes (60). The plurality of discharge electrodes (60) are arranged in a circumferential direction around the axis of the shaft body (31) or the axis of the spacer (40) (i.e., the shaft member (32)) about the axis (P). Each of the discharge electrodes (60) has an electrode body (65) and a tip end (63) formed at an end of the electrode body (65). The electrode body (65) has a rectangular plate-like base portion (61) and a tapered portion (62) having a substantially triangular plate shape and projecting radially outward from the base portion (61). The tip ends (63) are arranged at equal intervals in the circumferential direction around the axis (P) (with the pitch W shown in FIG. 6). Each of the tip ends (63) of the discharge electrodes (60) serves as a starting point of a streamer discharge.

As shown in FIG. 8, each of the discharge electrodes (60) forms a predetermined angle $\theta 1$ with respect to the support plate portion (51) (i.e., the plane (F) perpendicular to the axis (P)). Specifically, the discharge electrode (60) of this embodiment extends obliquely to approach the inner peripheral surface (21) of the counter electrode (20) as it goes toward the tip end (63). In other words, the angle $\theta 1$ is an acute angle with respect to the plane (F).

The plurality of discharge electrodes (60) arranged in the circumferential direction of each of the discharge members (50) constitute a single electrode row (L). In this embodiment, in the order from top to bottom, the first to fifth electrode rows (L1 to L5) are arranged at equal intervals (at intervals H shown in FIG. 8) in a direction along the axis (P).

Figure 6:
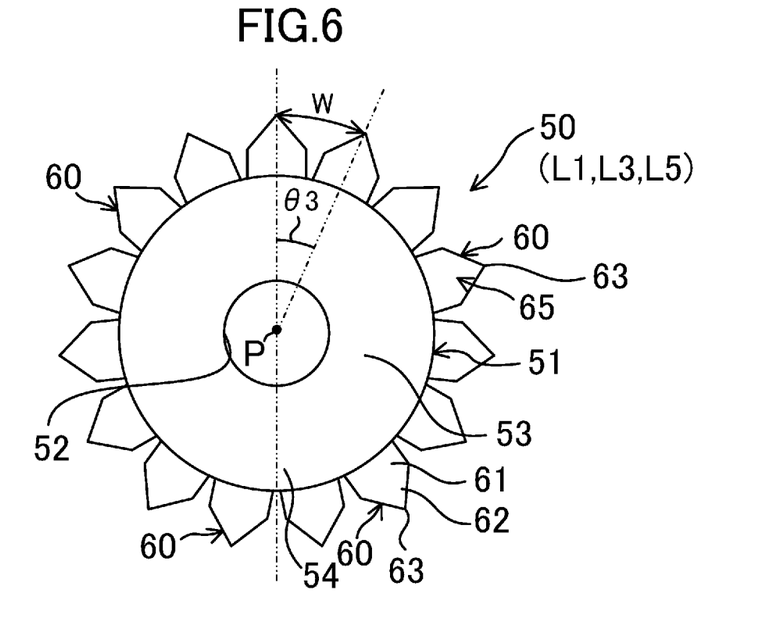
FIG. 6 is a plan view of a discharge member, in which a plurality of discharge electrodes are arranged at a first angular position.
Figure 7:
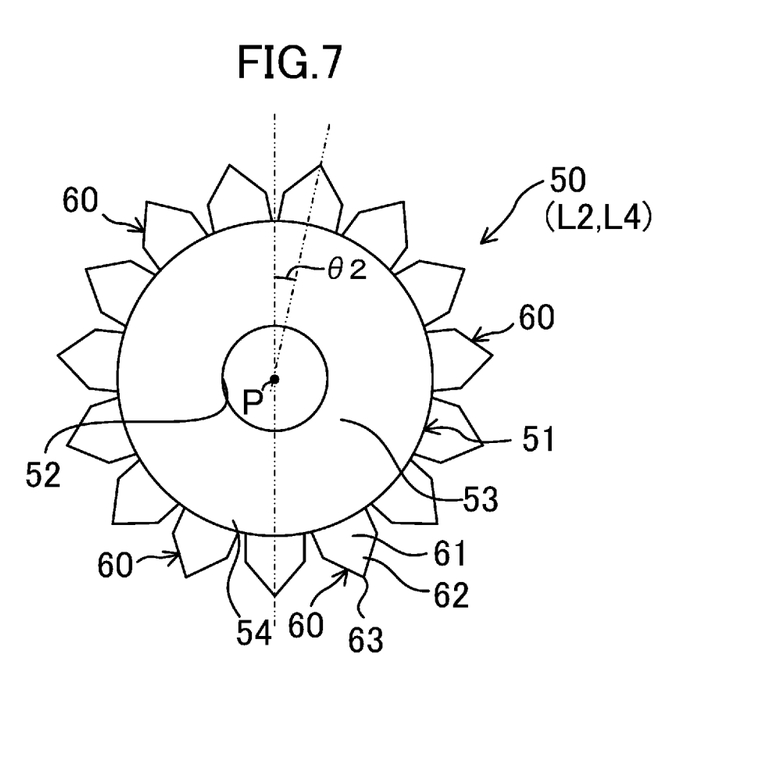
FIG. 7 is a plan view of a discharge member, in which a plurality of discharge electrodes are arranged at a second angular position misaligned with the first angular position in a circumferential direction.

As shown in FIGS. 6 and 7, in the present embodiment, each of the tip ends (63) of the plurality of discharge electrodes (60) of one of an adjacent pair of the electrode rows (L) and an associated one of the tip ends (63) of the plurality of discharge electrodes (60) of the other electrode row (L) are misaligned with each other in the circumferential direction when viewed along the axis (P). For example, the tip ends (63) of the discharge electrodes (60) of the first, third, and fifth electrode rows (L1), (L3), and (L5) (see, e.g., FIG. 6) and the associated tip ends (63) of the discharge electrodes (60) of the second and fourth electrode rows (L2) and (L4) (e.g., FIG. 7) are misaligned with each other in the circumferential direction by an angle θ2. In this embodiment, the angle θ2 is set to be half the angle difference θ3 (see FIG. 6) between the tip ends of the adjacent discharge electrodes (60). Thus, the distance between the tip ends (63) of the discharge electrodes (60) of the adjacent electrode rows (L) can be maximized. Note that the angle θ2 is merely an example, and may be any other value.

<Power Supply Unit>

The power supply unit (80) supplies a high direct current voltage (e.g., about 6.0 kV) to the discharge electrodes (60) and the counter electrode (20). The power supply unit (80) of the present embodiment has a single high-voltage direct current power supply (81). The positive electrode side of the power supply (81) is connected to a portion of the shaft body (31) between the upper and lower insulators (35). The counter electrode (20) is connected to the negative electrode side of the power supply (81). The negative electrode side of the power supply (81) is grounded. Thus, the discharge electrodes (60) serve as anode electrodes, and the counter electrode (20) serves as a ground electrode. The discharge electrodes (60) may be used as cathode electrodes.

—Operation and Action of Electric Discharge Device—

Next, the operation and action of the electric discharge device (10) will be described.

The electric discharge device (10) is operated while the air cleaner (1) is in operation. Air outside the case unit (11) flows into the air flow path (12) inside the case unit (11) through the plurality of inflow ports (15a). In the air flow path (12), the air flows upward along the discharge unit (30) and passes between the discharge electrodes (60) and the counter electrode (20).

In the electric discharge device (10), a voltage is applied from the power supply (81) to the discharge electrodes (60) and the counter electrode (20). Specifically, a voltage is supplied from the power supply (81) to the discharge electrodes (60) via the shaft body (31) and the spacers (40). As a result, as shown in FIGS. 8 and 9, a streamer discharge occurs from the tip end (63) of each discharge electrode (60) toward the inner peripheral surface (21) of the counter electrode (20).

The outer peripheral surfaces (43) of the spacers (40) are electrically connected to the discharge electrodes (60), and have the same polarity (e.g., positive) as the discharge electrodes (60). The outer peripheral surfaces (43) of the spacers (40) face the tip ends (63) of the discharge electrodes (60) and the inner peripheral surface (21) of the counter electrode (20). Specifically, each of the discharge electrodes (60) extends such that its tip end (63) and its electrode body (65) are misaligned with each other in the axial direction of the shaft body (31). Thus, a space (S) extending in a radial direction of the shaft body (31) (a direction along a plane perpendicular to the axis of the shaft body (31)) is formed around the outer peripheral surface (43) of the spacer (40) (see FIG. 8). With the provision of this space (S), the outer peripheral surface (43) of the spacer (40) functions as a discharge stabilizer which stabilizes the streamer discharge from the tip ends (63) of the discharge electrodes (60) toward the counter electrode (20). That is, the streamer discharge that occurs from the tip end (63) of each discharge electrode (60) does not travel toward the spacers (40) of the same polarity as the discharge electrodes (60), but is reversely directed toward the counter electrode (20). As a result, a uniform and stable radial streamer discharge occurs in the electric discharge device (10) as shown in FIG. 9. The streamer discharge causes active species to generate in the air. The active species is utilized for decomposing harmful substances (such as odor components and allergens) in the air.

Figure 9:
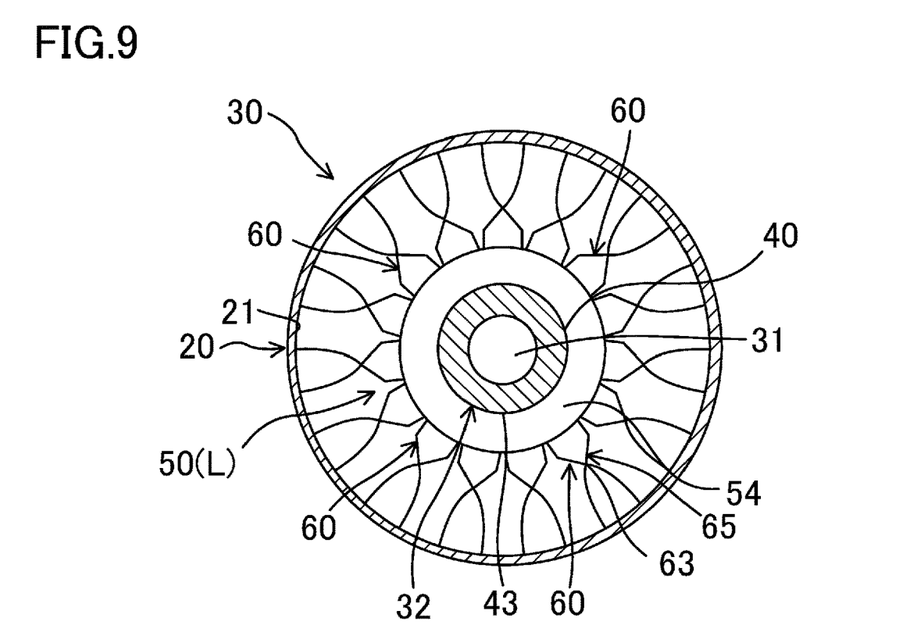
FIG. 9 is an enlarged cross-sectional view of a major portion of the discharge unit.

As shown in FIGS. 6, 7, and 9, the plurality of discharge electrodes (60) of the same electrode row (L) have their tip ends (63) arranged with an equal pitch in the circumferential direction. Further, the tip ends (63) of the discharge electrodes (60) are at the same distance from the inner peripheral surface (21) of the counter electrode (20), and also at the same distance from the outer peripheral surface (43) of the spacer (40). Therefore, the electric fields around all the discharge electrodes (60) are made uniform in the electric discharge device (10), which makes it possible to cause the radial streamer discharge more uniformly and stably.

As shown in FIG. 8, each of the discharge electrodes (60) extends obliquely to approach the inner peripheral surface (21) of the counter electrode (20) as it goes toward the tip end (63). Thus, the tip end (63) of each of the discharge electrodes (60) is closer to the axis (P) than, for example, a tip end of a discharge electrode of a comparative example (indicated by a chain double-dashed line E in FIG. 8) extending straight in a radially outward direction. Therefore, even if the inner peripheral surface (21) of the counter electrode (20) is made small, the distance between the tip ends (63) of the discharge electrodes (60) and the counter electrode (20) can be ensured. This can reduce the diameter and size of the counter electrode (20).

Further, when the tip ends (63) of the discharge electrodes (60) are melted due to the streamer discharge, the tip ends (63) of the discharge electrodes (60) are gradually shifted toward the base portions of the discharge electrodes. When the tip ends of the discharge electrodes E of the comparative example are shifted in this way, a distance G between the discharge electrodes (60) and the counter electrode (20) greatly varies. In contrast, when melted, the tip ends (63) of the discharge electrodes (60) of this embodiment are shifted obliquely toward the base portions of the discharge electrodes (60). Therefore, the distance G between the electrodes does not greatly vary due to the melting of the tip ends (63) of the discharge electrodes (60). This allows the streamer discharge to stably continue for a long time.

When the plurality of discharge electrodes (60) are arranged to extend obliquely, a distance (distance b in FIG. 8) from the tip ends (63) of the discharge electrodes (60) of one of an adjacent pair of the electrode rows (L) and the base end portions of the discharge electrodes (60) of the other electrode row (L) can be increased. This can reduce the interference between electric fields of the adjacent electrode rows (L), and the interval between the electrode rows (L) as well.

In this embodiment, as shown in FIGS. 6 and 7, the tip ends (63) of the discharge electrodes (60) of one of an adjacent pair of the electrode rows (L) are misaligned with the tip ends (63) of the discharge electrodes (60) of the other electrode row (L). This can further reduce the interference between the electric fields of the adjacent electrode rows (L), and the interval between the electrode rows (L) as well. The tip ends (63) of the discharge electrodes (60) of the adjacent electrode rows (L) may coincide with each other when viewed in the axial direction.

Advantages of Embodiment

According to this embodiment, a radial streamer discharge can be generated from the plurality of discharge electrodes (60) arranged in the circumferential direction toward the counter electrode (20), and the electric discharge device (10) which is compact and performs a stable streamer discharge can be provided. With the plurality of discharge electrodes (60) arranged in the circumferential direction, each discharge electrode (60) is sandwiched between other discharge electrodes (60). Further, the tip ends (63) of all the discharge electrodes (60) are at the same relative position with respect to the inner peripheral surface (21) of the counter electrode (20) and the outer peripheral surface (43) of the shaft member (32). Therefore, electric fields around the discharge electrodes (60) can be made uniform, and a uniform and stable radial streamer discharge can be achieved.

Variations of Embodiment

The electric discharge device (10) of the embodiment described above may be modified as follows.

<First Variation>

Figure 10:
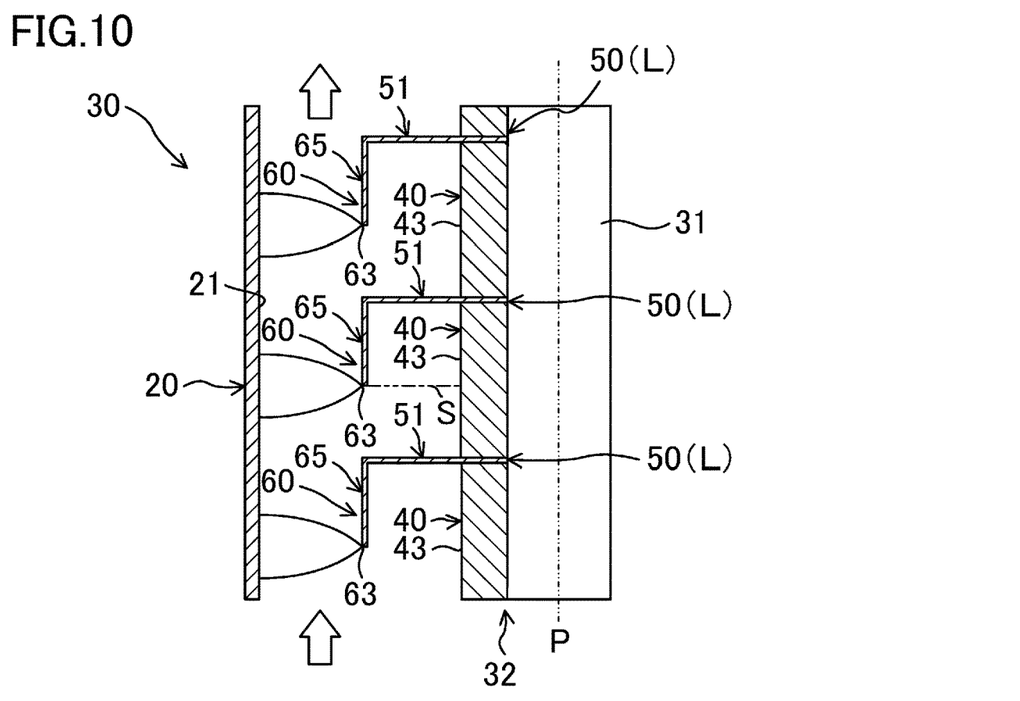
FIG. 10 is a view corresponding to FIG. 8 showing a first variation.

According to a first variation shown in FIG. 10, a plurality of discharge electrodes (60) extend along an axial direction (along an axis (P)) of an inner peripheral surface (21) of a counter electrode (20). Specifically, the plurality of discharge electrodes (60) extend in a direction perpendicular to a plane (F) perpendicular to the axis (P). Thus, the tip end (63) and electrode body (65) of each discharge electrode (60) are misaligned with each other in the axial direction, and a space (S) extending in a radial direction of the shaft body (31) (a direction along the plane perpendicular to the axis) is formed around the outer peripheral surface (43) of the spacer (40). As a result, the outer peripheral surface (43) of the spacer (40) functions as a discharge stabilizer which stabilizes a streamer discharge from the tip ends (63) of the discharge electrodes (60) toward the counter electrode (20).

Also in the first variation, the tip ends (63) of the discharge electrodes (60) are positioned close to the axis (P), which can reduce the diameter and size of the counter electrode (20). In addition, in the first variation, when the tip ends (63) of the discharge electrodes (60) are melted, the tip ends (63) are shifted toward the base portions of the discharge electrodes (60) in a direction along the outer peripheral surface (43) of the counter electrode (20). This can reliably avoid the distance between the discharge electrodes and the counter electrodes from varying due to the melting of the tip ends (63) of the discharge electrodes (60), and hence, allows a streamer discharge to occur stably for a long time.

<Second Variation>

Figure 11:
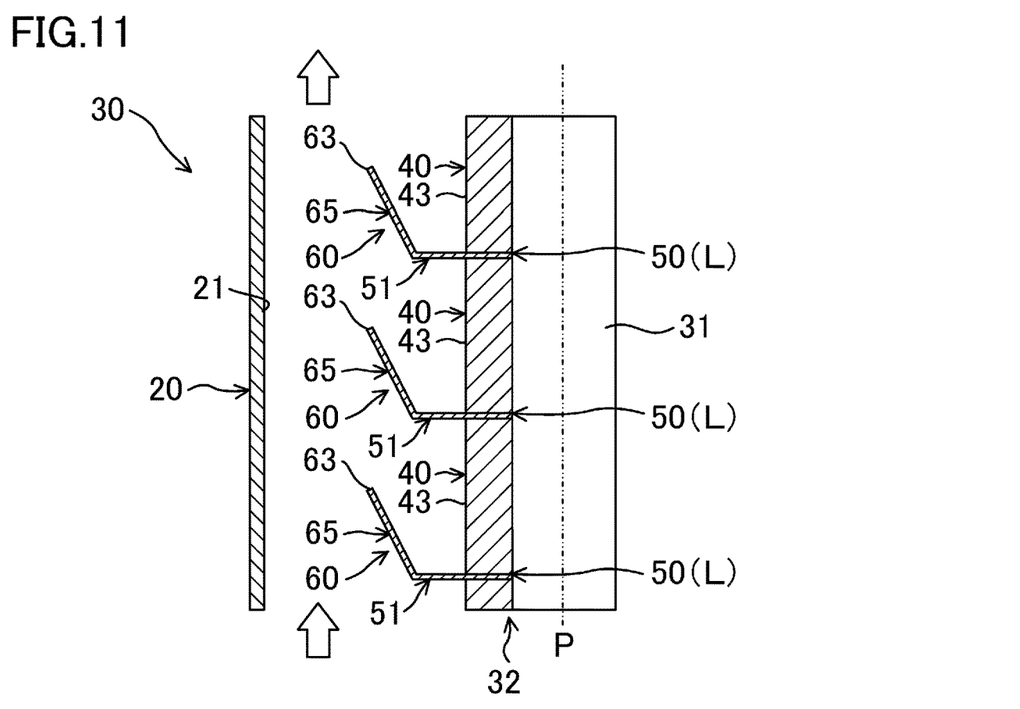
FIG. 11 is a view corresponding to FIG. 8 showing a second variation.

According to a second variation shown in FIG. 11, a plurality of discharge electrodes (60) extend obliquely toward the downstream side (for example, the upper side) in the air flow direction. Note that the discharge electrodes (60) may extend straight toward the downstream side (upward) in the air flow direction.

In the second variation, each discharge electrode (60) extends along the air flow direction. Therefore, each discharge electrode (60) is less likely to serve as a resistance in the air flow path (12). This can reduce the pressure loss of the air flow path (12).

Other Embodiments

The foregoing embodiment may also be modified in the following manner.

Each of the discharge electrodes (60) of the foregoing embodiment has been provided with a triangular plate-shaped or tapered portion. However, the discharge electrodes (60) may have the shape of a rod or a column having a uniform cross section. In this case, the cross-sectional shape of each discharge electrode (60) may be a circle, a rectangle, a triangle, a polygon, or the like. Further, the discharge electrode (60) may have a triangular plate-shaped or tapered base portion, and a rod- or column-shaped tip end portion having a uniform cross section at a protruding end thereof.

In the foregoing embodiment, the outer peripheral surface of the shaft member (32) (the outer peripheral surface (43) of the spacer (40)) and the inner peripheral surface (21) of the counter electrode (20) are formed in a cylindrical shape. However, the outer peripheral surface (43) of the shaft member (32) and the inner peripheral surface (21) of the counter electrode (20) may have a polygonal shape to face each other.

The electric discharge device (10) may be installed in an air conditioner for cooling or heating the air, or a humidity control apparatus for dehumidifying or humidifying the air, for example. The electric discharge device (10) can also be installed in a ventilator for ventilating the interior of the room. The air conditioner, the humidity control apparatus, and the ventilator are also included in the air purification device in a broad sense.

INDUSTRIAL APPLICABILITY

As can be seen from the foregoing description, the present invention is useful for an electric discharge device and an air purification device.

DESCRIPTION OF REFERENCE CHARACTERS

10 Electric Discharge Device
12 Air Flow Path
20 Counter Electrode
21 Inner Peripheral Surface
32 Shaft Member
43 Outer Peripheral Surface
60 Discharge Electrode
63 Tip End
65 Electrode Body
81 Power Supply
L Electrode Row

The invention claimed is:

1. An electric discharge device comprising: a shaft member; a plurality of discharge electrodes arranged in a circumferential direction around an axis of the shaft member; a cylindrical counter electrode in which the shaft member and the discharge electrodes are arranged; and a power supply applying a voltage to the discharge electrodes and the counter electrode, wherein
the shaft member has the same polarity as the discharge electrodes, a portion of the shaft member being comprised of a conductive resin material having the same polarity as the discharge electrodes,
each of the discharge electrodes has an electrode body and a tip end which is formed at an end of the electrode body facing an inner peripheral surface of the counter electrode, the discharge electrodes extending such that the tip end and the electrode body of each of the discharge electrodes are misaligned with each other in an axial direction of the shalt member, the voltage applied by the power supply causes a streamer discharge to travel from the tip ends of the discharge electrodes toward the inner peripheral surface of the counter electrode, the shaft member includes a shaft body and a cylindrical member made of the conductive resin material, the electric discharge device further comprises a discharge member including a support plate portion including an outer peripheral edge supporting the plurality of discharge electrodes, and the support plate portion includes a hole into which the shaft body is fitted.

2. The electric discharge device of claim 1, wherein a plurality of electrode rows each having the discharge electrodes arranged in the circumferential direction are arranged in the axial direction of the shaft member.

3. The electric discharge device of claim 1, wherein the discharge electrodes extend to form a predetermined angle with a plane perpendicular to the axis of the shaft member.

4. The electric discharge device of claim 2, wherein each of the discharge electrodes extends obliquely to approach the inner peripheral surface of the counter electrode as the discharge electrode goes toward the tip end.

5. The electric discharge device of claim 1, wherein the discharge electrodes extend along an axial direction of an outer peripheral surface of the counter electrode.

6. The electric discharge device of claim 3, wherein an air flow path through which air flows in the axial direction of the shaft member is formed between the shaft member and the counter electrode, and the discharge electrodes extend so that the tip ends face toward a downstream side in a flow direction of the air.

7. The electric discharge device of claim 2, wherein the tip ends of the discharge electrodes in one of the electrode rows and the tip ends of the discharge electrodes of another electrode row adjacent to the one of the electrode row are misaligned with each other in a circumferential direction when viewed in the axial direction of the shaft member.

8. The electric discharge device of claim 1, wherein the tip ends of the discharge electrodes are arranged at equal intervals around the axis of the shaft member.

9. An air purification device comprising the electric discharge device of claim 1.

* * * * *